United States Patent [19]

Kochanny, Jr. et al.

[11] 3,971,730
[45] July 27, 1976

[54] CHLORINATING COMPOSITION OF CHLORINE MONOXIDE IN 1,1,1-TRICHLOROETHANE

[75] Inventors: Gerald L. Kochanny, Jr.; Thomas A. Chamberlin, both of Midland, Mich.

[73] Assignee: The Dow Chemical Company, Midland, Mich.

[22] Filed: Sept. 9, 1974

[21] Appl. No.: 504,020

Related U.S. Application Data

[60] Division of Ser. No. 281,475, Aug. 17, 1972, Pat. No. 3,872,176, which is a continuation-in-part of Ser. No. 799,484, Feb. 14, 1969, abandoned.

[52] U.S. Cl. .................... 252/187 R; 204/163 R; 260/658 R; 423/462
[51] Int. Cl.² ......................................... C01B 11/02
[58] Field of Search ............ 252/187 R; 260/658 R; 204/163 R; 423/462

[56] References Cited

UNITED STATES PATENTS

| 3,012,081 | 12/1961 | Conrad et al. ................. 260/658 R |
| 3,019,175 | 1/1962 | Haefner et al. ................ 260/658 R |

OTHER PUBLICATIONS

Tanner et al., JACS 89, 1967, pp. 121–125.

*Primary Examiner*—Benjamin R. Padgett
*Assistant Examiner*—Irwin Gluck
*Attorney, Agent, or Firm*—L. Wayne White

[57] ABSTRACT

1,1,1-Trichloroethane is prepared in the novel process comprising reacting by contacting chlorine monoxide with $CH_3-CH_2Cl$ and/or $CH_3-CHCl_2$. The reaction is conducted in liquid phase and at a temperature of from about $-20°$ to about $80°C$.

1 Claim, No Drawings

CHLORINATING COMPOSITION OF CHLORINE MONOXIDE IN 1,1,1-TRICHLOROETHANE

CROSS-REFERENCE TO RELATED APPLICATION

This application is a division of our copending application Ser. No. 281,475 filed Aug. 17, 1972, now U.S. Pat. No. 3,872,176 which is a continuation-in-part of our application Ser. No. 799,484 filed Feb. 14, 1969 (now abandoned).

BACKGROUND OF THE INVENTION 1,1,1-Trichloroethane is a known compound which is commercially used as a solvent.

There are several known methods for preparing the compound. The most common methods comprise chlorinating chloroethane (or 1,1-dichloroethane) with chlorine under special conditions. For example, Haefner et al. (U.S. Pat. No. 3,019,175) teach that chlorine reacts with 1,1-dichloroethane in the presence of actinic light and in certain directive chlorination solvents (e.g. $CS_2$) to produce 1,1,1-trichloroethane.

The problem with such prior art processes is that they produce acidic by-products (such as HCl) and considerable amounts of 1,2-polychlorinated ethanes in addition to the desired product. Such contaminants are undesirable and have to be removed, typically by acid scrubbers and a distillation step. Economically, the 1,2-polychlorinated ethanes thus produced are undesirable because the commercial market for them is currently quite small.

A need therefore exists for a method of manufacturing 1,1,1-trichloroethane essentially free of 1,2-polychlorinated ethanes.

SUMMARY OF THE INVENTION

A new process has now been discovered wherein 1,1,1-trichloroethane is prepared in excellent yields and purity, i.e. substantially free of 1,2-polychlorinated ethanes. The novel process comprises reacting by contacting in liquid phase chlorine monoxide ($Cl_2O$) with chloroethane and/or 1,1-dichloroethane.

Our discovery that $Cl_2O$ would selectively chlorinate chloroethane and/or 1,1-dichloroethane was most surprising in view of Tanner et al. (J. Am. Chem. Soc. 89, 121 (1967)).

Tanner et al. produced dichloropropanes and dichlorobutanes by contacting (a) $Cl_2O$ and (b) 1-chloropropane or 1-chlorobutane in a molar ratio of 1 mole of (c) per 10 moles of (b). The reaction was conducted in $CCl_4$ solvent and in the presence of actinic light. Attempts to run the reaction in the dark and/or in the presence of atmospheric amounts of oxygen were unsuccessful in that the reaction rate was much too low to be practical. Tanner et al. obtained in every instance a mixture of dichloropropanes (or dichlorobutanes). Tanner et al. did not report and apparently did not observe any 1,1,1-trichloropropane or any 1,1,1-trichlorobutane (or any other trichlorinated isomer) produced in the course of the reaction. Such data are unexpectedly contradictory to the results we observe in the reaction of $Cl_2O$ with chloroethane and/or 1,1-dichloroethane, the adjacent homolog.

Our novel reaction is represented by the equations:

(i)  $CH_3-CH_2Cl + Cl_2O = CH_3-CCl_3 + H_2O$
       (I)                    (III)

(ii) $2CH_3-CHCl_2 + Cl_2O = CH_3-CCl_3 + H_2O$.

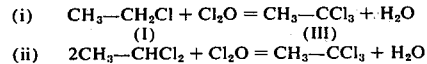

We prefer to conduct the reaction under substantially anhydrous conditions since water lowers the reaction rate and reacts with $Cl_2O$ to produce HOCl. The latter compound is far less selective chlorinating agent than $Cl_2O$ in the instant process and could produce undesirable isomers in competing side reactions. Under substantially anhydrous conditions, little if any acidic by-product is formed and the special equipment (e.g. acid scrubbers) needed in the prior art processes can be eliminated. This is a substantial economic and procedural advantage.

The water formed during the course of the reaction is easily removed by conventional means. E.g. water can be removed by (1) conducting the reaction in the presence of a dehydrating agent, e.g. $Na_2SO_4$, $CaSO_4$ and others in the known class of drying agents, (2) azeotropic distillation, (3) physical liquid-liquid phase separation, or by other methods known to those skilled in the art.

We have discovered that $Cl_2O$ selectively chlorinates the 1-carbon atom of 1-chloroethane and 1,1-dichloroethane under any set of conditions wherein the rate of chlorination is higher than the rate of thermal and/or photo-initiated decomposition of $Cl_2O$. For this reason, the reaction is preferably conducted in the dark (or substantial absence of actinic light) and at a temperature where the rate of thermal decomposition of $Cl_2O$ is relatively low.

By actinic light is meant radiation of short wave length, as occurs in the visible and ultraviolet portion of the spectrum, that possesses sufficient energy to cause chemical reaction. $Cl_2O$ decomposes rapidly in the presence of actinic light to form an unresolved mixture of products which include chlorine, free radicals of chlorine and other chlorine-containing species. Various species in this unresolved mixture are nonselective chlorinating agents in the reaction with 1-chloroethane and/or 1,1-dichloroethane.

The rate of thermal decomposition of $Cl_2O$ increases with increasing temperatures, and above about 140°C $Cl_2O$ has been known to decompose explosively. The thermal decomposition products are a similar unresolved mixture of nonselective chlorinating agents.

A suitable reaction temperature is one sufficiently low that the rate of thermal decomposition is lower than the rate of chlorination and yet is sufficiently high to promote the chlorination reaction. A reaction temperature between about −20°C and about 80°C is generally satisfactory. A preferred temperature range is from about 0° to about 50°C and the most preferred temperature range is from about 10°C to about 40°C.

At temperatures in the lower portion of the suitable temperature range, e.g. 0°C, and in the absence of actinic light, the selectivity of $Cl_2O$ in the subject process is very high, almost quantitative, but the rate of chlorination is low. At higher temperatures, such as 50°C and above, the degree of selectivity of $Cl_2O$ in the subject reaction is lower but the rate of chlorination is substantially increased.

The stoichiometry of the reaction is shown by equations (i) and (ii) above. Substantially any molar ratio of reactants can be used (e.g. from about 1:20 to about 20:1). However, in order to maximize the production of $CH_3-CCl_3$, we prefer to use a stoichiometric amount or excess of $Cl_2O$ (e.g. up to about a 5-fold excess) and we most prefer to use a stoichiometric amount of $Cl_2O$.

The reaction time varies inversely with the temperature and therefore may vary from a few minutes to several days. Accordingly, the reactants should be maintained in contact with each other until the desired reaction product is formed.

The reaction is conducted in liquid phase, which means that gaseous or liquid $Cl_2O$ may be admixed with liquid $CH_3$—$CH_2Cl$ and/or $C_3$—$CHCl_2$ either alone or in solution in an inert liquid. 1,1,1-Trichloroethane is inert in the reaction and is the preferred solvent, if a solvent or diluent is used. Other suitable solvents include perhalogenated hydrocarbons, e.g. $CCl_4$.

Pressure on the reaction is not critical so long as the reaction medium is liquid.

The atmosphere above the reaction mixture may surprisingly contain oxygen without detriment to the reaction rate and selectivity of $Cl_2O$ in the subject reaction. An inert gas, such as nitrogen, may also be used.

SPECIFIC EMBODIMENTS

The following examples further illustrate the invention:

EXAMPLE 1

Reaction of $Cl_2O$ with $CH_3CH_2Cl$ (Neat)

$Cl_2O$ (gas) was generated according to the method of Cady (1) and dissolved in ethyl chloride at −78°C over a period of 2 hours. During this time, the concentration of $Cl_2O$ rose to 3.4 Molar. Portions of this reaction mixture were removed, placed in stoppered vessels (containing air above the mixture) and allowed to react further at various temperatures as indicated in Table I. The reactions were conducted under ordinary laboratory lighting and no precautions were taken to exclude actinic light from entering the reacting mixtures. The reaction times in Table I are exclusive of the above 2 hour dissolution period. The mole percentages of materials were measured by means of vapor phase chromatography (v.p.c.).

TABLE I

| No. | Reaction Time (Hrs.) | Reaction Temp. (°C) | A* | B | C | D | E |
|---|---|---|---|---|---|---|---|
| 1 | 7.0 | −78 | 82.7 | 9.96 | 0.76 | 1.37 | 0.11 |
| 2 | 3.5 | 25 | 52.8 | 28.40 | 7.46 | 3.51 | 0.41 |

TABLE I-continued

| No. | Reaction Time (Hrs.) | Reaction Temp. (°C) | A* | B | C | D | E |
|---|---|---|---|---|---|---|---|
| 3 | 30.0 | 25 | 36.4 | 41.20 | 11.04 | 9.99 | 1.41 |

*wherein:
A = $CH_3CH_2Cl$ (mol.%)
B = $CH_3CHCl_2$ (mol.%)
C = $CH_3CCl_3$ (mol.%)
D = $ClCH_2CH_2Cl$ (mol.%)
E = $ClCH_2CHCl_2$ (mol.%)
(1) G. H. Cady, Inorganic Synthesis V 156 (1957).

EXAMPLE 2

Reaction of $Cl_2O$ with $CH_3CH_2Cl$ ($CCl_4$ solution)

A stock solution of $Cl_2O$ was prepared by dissolving $Cl_2O$ (gas), generated as described in Example I, in $CCl_4$ at 0°C to a 1.444 Molar concentration. A reaction mixture having equimolar amounts of $Cl_2O$ and $CH_3CH_2Cl$ was prepared by mixing 0.0488 moles of $CH_3CH_2Cl$ with a 31 ml. aliquot of the above $Cl_2O$—$CCl_4$ solution. Portions of the reaction mixture were allowed to react at various temperatures, in the dark, and in vessels open to the atmosphere. The results are summarized in Table II.

TABLE II (Molar Ratio $Cl_2O:CH_3CH_2Cl$ = 1:1)

| No. | Rxn. Time (Hrs.) | Rxn. Temp. (°C) | A* | B | C | D | E | F |
|---|---|---|---|---|---|---|---|---|
| 1 | 162 | 0 | 29.50 | 30.85 | 38.84 | 0.66 | 0.16 | — |
| 2 | 6 | 25 | 33.20 | 32.13 | 33.62 | 1.05 | — | — |
| 3 | 332 | 25 | 3.59 | 13.46 | 78.77 | 3.19 | 0.95 | 0.04 |
| 4 | 1 | 40 | 29.76 | 32.06 | 36.82 | 1.05 | 0.30 | — |
| 5 | 67 | 40 | 4.03 | 14.90 | 77.89 | 2.07 | 0.75 | 0.35 |

*wherein:
A = $CH_3CH_2Cl$ (mol.%)
B = $CH_3CHCl_2$ (mol.%)
C = $CH_3CCl_3$ (mol.%)
D = $ClCH_2CH_2Cl$ (mol.%)
E = $ClCH_2CHCl_2$ (mol.%)
F = others (mol.%)

EXAMPLE 3

Reaction of $Cl_2O$ with $CH_3CH_2Cl$ ($CCl_4$ solution)

Using substantially the same procedure as in Example 2, ethyl chloride was mixed with a stock solution of $Cl_2O$ in $CCl_4$ (0.406 M) to form a reaction mixture wherein the molar ratio of $Cl_2O:CH_3CH_2Cl$ = 1:10. Portions of the reaction mixture were placed in glass ampoules, cooled to −196°C, evacuated to about 4×10$^{-4}$ mm of Hg, sealed and then allowed to react at various temperatures in the dark. The results are summarized in Table III.

TABLE III (Molar Ratio $Cl_2O:CH_3CH_2Cl$ = 1:10)

| No. | Rxn. Time (Hrs.) | Rxn. Temp. (°C) | A* | B | C | D |
|---|---|---|---|---|---|---|
| 1 | 6 | 25 | 90.01 | 8.99 | 0.61 | 0.39 |
| 2 | 24 | 25 | 86.17 | 12.16 | 1.14 | 0.53 |
| 3 | 1 | 40 | 90.66 | 8.47 | 0.36 | 0.52 |
| 4 | 24 | 40 | 82.96 | 14.13 | 1.45 | 1.46 |

*wherein:
A = $CH_3CH_2Cl$ (mol.%)
B = $CH_3CHCl_2$ (mol.%)
C = $CH_3CCl_3$ (mol.%)
D = $ClCH_2CH_2Cl$ (mol.%)

EXAMPLE 4

Reaction of $Cl_2O$ with $CH_3CH_2Cl$ ($CCl_4$ solution)

Using substantially the same procedure as in Example 3, ethyl chloride was mixed with a stock solution of $Cl_2O$ in $CCl_4$ (1.668 M) to form a reaction mixture wherein the molar ratio of $Cl_2O:CH_3CH_2Cl = 10:1$. Portions of the reaction mixture were allowed to react in ampoules filled as per Example 3 at various temperatures in the dark. The results are summarized in Table IV.

TABLE IV (Molar Ratio $Cl_2O:CH_3CH_2Cl = 10:1$)

| No. | Rxn. Time (Hrs.) | Rxn. Temp. (°C) | A* | B | C |
|---|---|---|---|---|---|
| 1 | 6 | 25 | 1.49 | 1.62 | 96.89 |
| 2 | 24 | 25 | — | — | 100.0 |
| 3 | 1 | 40 | 8.70 | 10.62 | 80.68 |
| 4 | 24 | 40 | — | — | 100.0 |

*wherein:
A = $CH_3CH_2Cl$ (mol.%)
B = $CH_3CHCl_2$ (mol.%)
C = $CH_3CCl_3$ (mol.%)

EXAMPLE 5

$Cl_2O$ vs. $Cl_2$ in Chlorination Reaction

A series of reactions were conducted to compare the selectivity of $Cl_2O$ and $Cl_2$ as chlorinating agents. The reaction conditions were: (a) 25°C; (b) inert atmosphere ($N_2$); (c) reactants in solution with $CCl_4$ (or $CF_2Cl-CFCl_2$); (d) sealed glass ampoules, and (e) molar ratio of chlorinating agent to substrate = 1:10. Some reactions were conducted in the presence of light supplied by a 250 watt General Electric Sun Lamp placed 10 inches from the reaction vessels. Other reactions were conducted in the dark. The reaction mixtures were prepared by mixing together solutions of substrate and chlorinating agent in $CCl_4$. Each reaction was run to completion, i.e., until the chlorinating agent was consumed. The reaction products were analyzed by v.p.c. and the results summarized in Table V.

TABLE V

| Chlorinating Agent Substrate | Product Ratio | $Cl_2$/hν | $Cl_2O$/hν | $Cl_2O$/dark |
|---|---|---|---|---|
| $CH_3CH_2Cl$ | $CH_3CH_2Cl_2$ / $ClCH_2CH_2Cl$ | 54.2 / 45.8 | 71.0 / 29.0 | 97.8 / 2.2 |
| $CH_3CHCl_2$ | $CH_3CCl_3$ / $ClCH_2CHCl_2$ | 79.5 / 20.5 | 90.0 / 10.0 | 99.8 / 0.2 |
| $ClCH_2CHCl_2$ | $ClCH_2CCl_3$ / $Cl_2CHCHCl_2$ | 41.8 / 58.2 | 60.5 / 39.5 | 84.7 / 15.3 |

The products named under "Product Ratio" above in Table V were the only products observed via v.p.c. except for trace amounts of other unidentified products in the chlorination of $ClCH_2CHCl_2$.

Substantially the same results were obtained when the $Cl_2O$/dark experiments were duplicated except the atmosphere was air rather than nitrogen.

EXAMPLE 6

Reaction of $Cl_2O$ with $CH_3CHCl_2$ ($CCl_4$ solution)

To compare the effect of dehydrating agents upon the reaction rate, solutions of $Cl_2O$ and $CH_3CHCl_2$ in $CCl_4$ were prepared such that the ratio of $Cl_2O:CH_3CHCl_2$ was 1:2. Both reaction mixtures were degassed and sealed in glass ampoules, as described in Example 3. In one ampoule, a slight excess of an anhydrous $Na_2SO_4$ was included as a dehydrating agent. The reaction mixtures were then allowed to warm to 25°C and maintained at that temperature until the half-life of the reaction was determined, i.e., the time period over which the initial concentration of $Cl_2O$ was decreased by 50 percent. The results are summarized in Table VI.

TABLE VI

| $Cl_2O$* (mols./liter) | $CH_3CHCl_2$* (mols./liter) | Dehydrating Agent | Half-Life (Hrs.) |
|---|---|---|---|
| 0.269 | 0.645 | none | 17.0 |
| 0.392 | 0.692 | $Na_2SO_4$ | 0.8 |

*Initial concentration in $CCl_4$.

We claim:
1. A liquid chlorinating composition comprising chlorine monoxide dissolved in 1,1,1-trichloroethane.

* * * * *